(12) United States Patent
Kobayashi et al.

(10) Patent No.: US 6,344,118 B1
(45) Date of Patent: Feb. 5, 2002

(54) STRUCTURE OF OXYGEN SENSING ELEMENT

(75) Inventors: Kiyomi Kobayashi, Kuwana; Namitsugu Fujii, Yokkaichi; Yasumichi Hotta, Mie-ken; Hiromi Sano, Nagoya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/130,902

(22) Filed: Aug. 7, 1998

(30) Foreign Application Priority Data

Aug. 7, 1997 (JP) ............................................. 9-227480

(51) Int. Cl.$^7$ ............................................. G01N 27/26
(52) U.S. Cl. ...................... 204/424; 204/421; 73/35.02; 73/23.32
(58) Field of Search ................................ 204/421, 422, 204/424; 73/31.05, 35.02, 23.32

(56) References Cited

U.S. PATENT DOCUMENTS

| 4,121,988 A | | 10/1978 | Sano et al. ............... 204/195 S |
|---|---|---|---|
| 4,199,425 A | | 4/1980 | Sinkevitch .............. 204/195 S |
| 4,220,516 A | | 9/1980 | Sano et al. ............... 204/195 S |
| 4,276,142 A | * | 6/1981 | Topp et al. ................. 204/429 |
| 4,356,065 A | * | 10/1982 | Dietz ......................... 205/783 |
| 4,379,741 A | * | 4/1983 | Sano et al. ................. 204/424 |
| 4,402,820 A | | 9/1983 | Sano et al. ................. 204/425 |
| 4,626,337 A | * | 12/1986 | Hotta et al. ................. 204/429 |
| 5,538,612 A | | 7/1996 | Kojima et al. .............. 204/429 |

FOREIGN PATENT DOCUMENTS

| EP | 0 345 770 | 12/1989 |
|---|---|---|
| EP | 0 809 101 | 11/1997 |
| GB | 2 297 169 | 7/1996 |
| JP | 8-271474 | 10/1996 |

\* cited by examiner

*Primary Examiner*—T. Tung
*Assistant Examiner*—Alex Noguerola
(74) *Attorney, Agent, or Firm*—Pillsbury Winthrop (57) ABSTRACT

An improved structure of an oxygen sensing element installed in an oxygen sensor designed to measure an oxygen content in gases is provided. The structure includes a cup-shaped solid electrolyte body, an inner electrode, and an outer electrode. The solid electrolyte body has a portion exposed to the gases which has a given length. The inner electrode is formed on an inner wall of the solid electrolyte body and exposed to air. The outer electrode is formed on an outer wall of the solid electrolyte body and exposed to the gases through a protective layer. The oxygen content in the gases is measured based on output signals from the inner and outer electrodes. The outer electrode occupies an area on the outer wall of the solid electrolyte body within a range of 80% of the given length of the gas-exposed portion of the solid electrolyte body and has a thickness ranging from 1.2 to 3.0 $\mu$m. This allows the oxygen sensing element to determine the oxygen content in the gases precisely and to have an improved heat-resistance.

18 Claims, 6 Drawing Sheets

| SAMPLE | THICKNESS OF HEAD ELECTRODE A (μm) | THICKNESS OF BASE ELECTRODE B (μm) | B/A | OUTPUT (V) | | HEAT RESISTANCE |
|---|---|---|---|---|---|---|
| 1 | 1.5 | 1.0 | 0.67 | 0.75 | ○ | ○ |
| 2 | 2.0 | 0.5 | 0.25 | 0.74 | ○ | ○ |
| 3 | 1.5 | 0.5 | 0.33 | 0.78 | ○ | ○ |
| 4 | 1.6 | 0.8 | 0.50 | 0.76 | ○ | ○ |
| 5 | 1.4 | 0.8 | 0.57 | 0.78 | ○ | ○ |
| 6 | 2.0 | 1.0 | 0.50 | 0.65 | ○ | ○ |
| 7 | 1.3 | 1.0 | 0.77 | 0.76 | ○ | ○ |
| 8 | 2.5 | 1.5 | 0.60 | 0.65 | ○ | ○ |
| 9 | 2.4 | 1.2 | 0.50 | 0.69 | ○ | ○ |
| 10 | 1.6 | 1.2 | 0.75 | 0.73 | ○ | ○ |
| 11 | 1.0 | 0.8 | 0.80 | 0.78 | ○ | × |
| 12 | 1.2 | 1.0 | 0.83 | 0.74 | ○ | × |
| 13 | 3.5 | 0.8 | 0.23 | 0.60 | × | ○ |
| 14 | 5.0 | 1.0 | 0.20 | 0.58 | × | ○ |

STRUCTURE OF OXYGEN SENSING ELEMENT

BACKGROUND OF THE INVENTION

1. Technical Field of the Invention

The present invention relates generally to an improvement on an oxygen sensing element which may be used in an oxygen sensor installed in an exhaust system of an internal combustion engine for automotive vehicles to measure an oxygen content in exhaust gases.

2. Background of Related Art

For burning control of fuel, an air-fuel ratio sensor is installed in an exhaust system of an engine for automotive vehicles to measure an air-fuel ratio. Such an air-fuel ratio sensor is usually implemented with an oxygen sensor having disposed therein an oxygen sensing element made of a solid electrolyte having an oxygen ion conductivity.

Such an oxygen sensor device is known in the art consists of a cup-shaped solid electrolyte body having an atmospheric chamber defined therein, an outer electrode disposed on an outer surface thereof, and an inner electrode disposed on an inner surface thereof exposed to the atmospheric chamber. The structure also has a ceramic heater installed in the atmospheric chamber to heat the oxygen sensing element up to an activating temperature quickly.

The outer electrode is formed by applying a conductive paste made of noble metallic powder dispersed in an organic binder to the outer surface of the solid electrolyte body and baking the conductive paste.

The outer electrode may alternatively be formed using another technique such as chemical plating, chemical vapor deposition, or physical vapor deposition.

In recent years, the oxygen sensing element having the electrodes formed in the manner, as described above, has been highlighted for high output and found to be suitable for use in oxygen sensors which are required to provide high outputs, especially within a low temperature range below 400° C.

Usually, a conductive paste is baked at 1400 to 1500° C., while a chemically plated layer is baked at 800 to 1000° C. The chemical plating, thus, realizes a high-output sensor with improved catalytic activity. The reason why the baking temperature of the conductive paste is higher than that of the chemically plated layer is that it is necessary to bake platinum powder having a grain size of the order of 0.5 to 1.0 $\mu$m.

The outer electrode with the improved catalytic activity formed using the chemical plating has, however, the following drawbacks.

Figure 1:
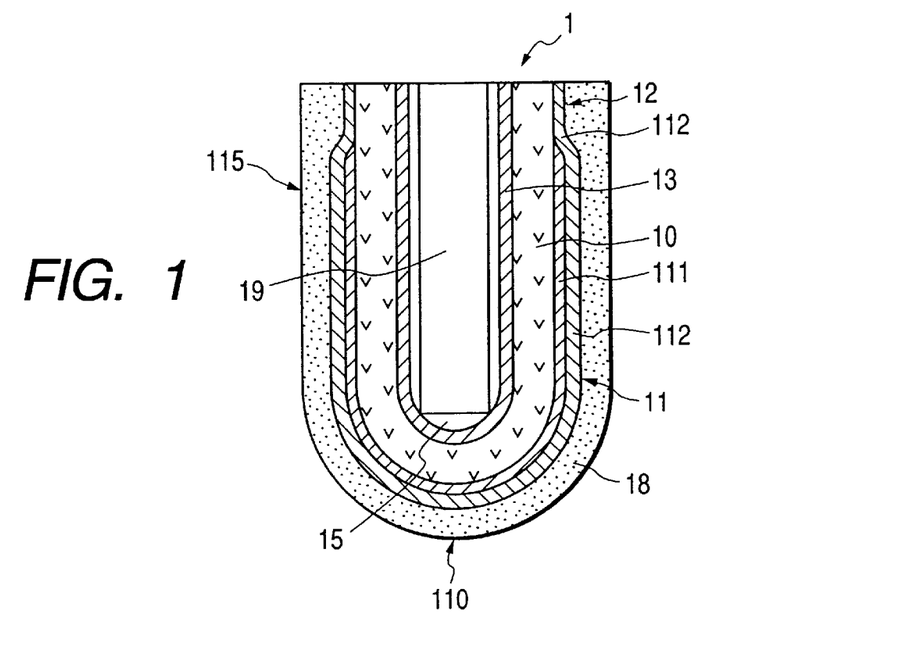
FIG. 1 is a partially cross sectional view which shows an oxygen sensing element according to the invention.
Figure 4:
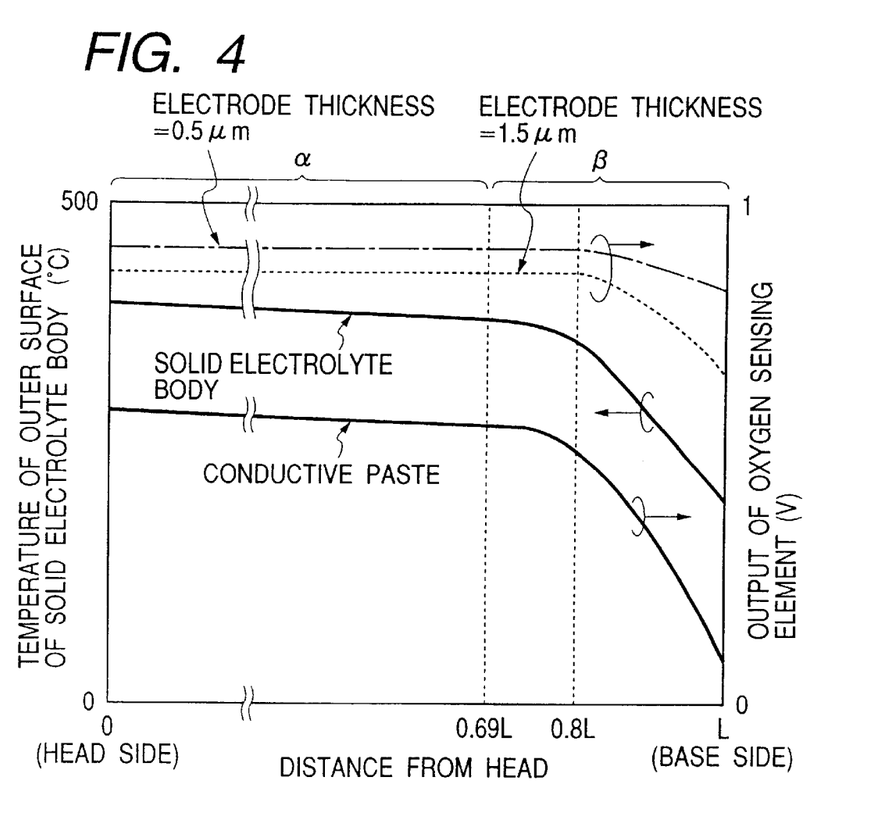
FIG. 4 is a graph which shows a relation between the outer surface temperature measured at a portion of a solid electrolyte body of an oxygen sensing element and the distance to the portion of the solid electrolyte body from the head thereof.

FIG. 4 illustrates a relation between outer surface temperature measured at a portion of a solid electrolyte body of an oxygen sensing element and distance to the portion of the solid electrolyte body from the head thereof. The relation shows that the outer surface temperature of the solid electrolyte is substantially constant around the head thereof, while it is decreased suddenly over a given boundary to a base of the solid electrolyte body. This is because a portion of the oxygen sensor element facing a ceramic heater, as shown in FIG. 1, is heated uniformly, while the other portion apart from the ceramic heater is lower in temperature. Thus, the output from the base of the outer electrode formed in the chemical plating is, as can be seen from the drawing, higher than that from an electrode made of a conductive paste in both cases where the thickness of the outer electrode is 0.5 $\mu$m and 1.5 $\mu$m. The total output from the outer electrode is actually the sum of outputs from the head and base thereof, but the output from the base of the outer electrode will be lower than that from the head when the base is smaller in thickness than the head, so that the output from the oxygen sensing element may be insufficient for functioning properly.

In recent years, the temperature at which the oxygen sensing element is used is more increased, resulting in exacerbation in the above problem. Specifically, an increase in ambient temperature will cause a difference in temperature between the head and base of the oxygen sensing element to be increased, resulting in a great difference in outputs therebetween. The total output from the oxygen sensing element, thus, depends greatly upon the output from the base thereof.

The use of a ceramic heater producing a large quantity of heat enough to raise the temperature the whole of the outer electrode uniformly may be proposed, but it may cause the overall temperature of the oxygen sensing element to be increased more than the temperature a filter, leads, and heater solder can withstand.

SUMMARY OF THE INVENTION

It is therefore a principal object of the present invention to avoid the disadvantages of the prior art.

It is another object of the present invention to provide an improvement on an oxygen sensing element capable of measuring an oxygen content in gasses with high accuracy.

According to one aspect of the present invention, there is provided an oxygen sensing element for measuring an oxygen content in gases which comprises: (a) a cup-shaped solid electrolyte body having a portion exposed to the gases which has a given length; (b) an inner electrode formed on an inner wall of the solid electrolyte body to provide an output signal; and (c) an outer electrode formed on an outer wall of the solid electrolyte body to provide an output signal for determining the oxygen content in the gases based on the output signals from the inner and outer electrodes. The outer electrode occupies an area on the outer wall of the solid electrolyte body within a range of 80% of the given length of the gas-exposed portion of the solid electrolyte body and has a thickness ranging from 1.2 to 3.0 $\mu$m.

In the preferred mode of the invention, a second outer electrode is further provided which is formed on a portion of the outer wall of the solid electrolyte body adjacent to the outer electrode and which has a thickness smaller than that of the outer electrode.

The thickness of the second outer electrode is within a range from 0.3 to 2.4 $\mu$m.

The ratio of the thickness of the second outer electrode to the thickness of the outer electrode is within a range of 0.25 to 0.8.

BRIEF DESCRIPTION OF THE DRAWINGS

The present invention will be understood more fully from the detailed description given hereinbelow and from the accompanying drawings of the preferred embodiment of the invention, which, however, should not be taken to limit the invention to the specific embodiment but are for explanation and understanding only.

In the drawings:

FIGS. 2(*a*) and 2(*b*) are perspective views which show structures of head and base electrodes of the oxygen sensing element of FIG. 1;

DESCRIPTION OF THE PREFERRED EMBODIMENT

Figure 2A:
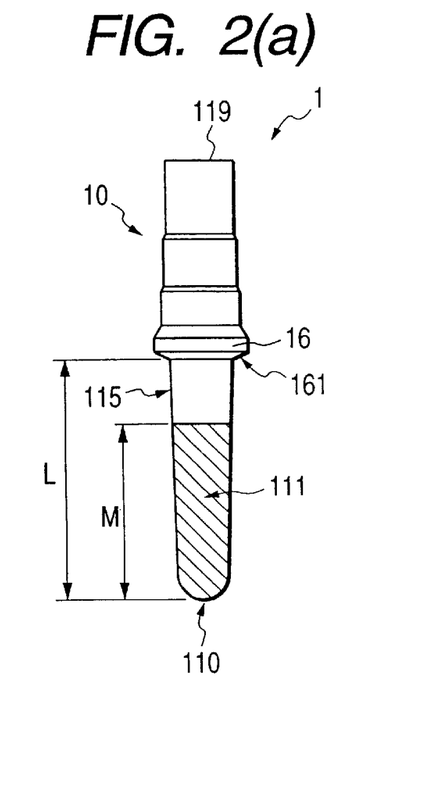
Figure 2B:
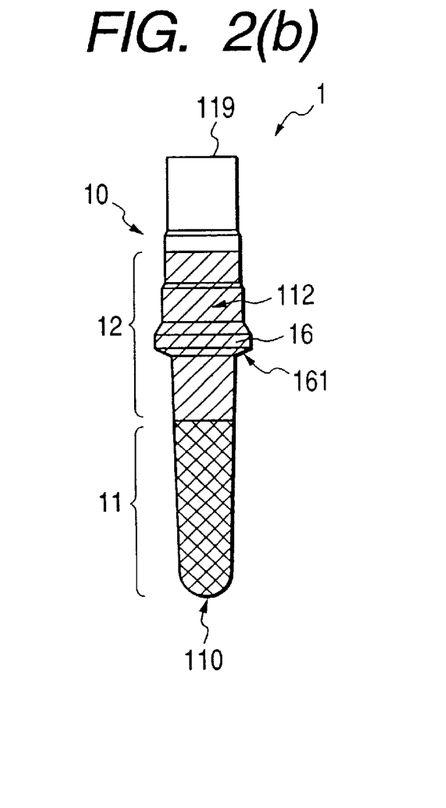

Referring now to the drawings, particularly to FIGS. 1, 2(a), and 2(b), there is shown an oxygen sensing element 1 for use in an oxygen sensor installed in an exhaust system of an automotive internal combustion engine to measure an oxygen content in exhaust gases using an oxygen concentration dependent electromotive force or a limiting current.

The oxygen sensing element 1 includes generally a cup-shaped solid electrolyte body 10 and a head electrode 11 made of a metallic material with high catalytic activity such as Pt, Ru, Pd, Rh, or Re. The head electrode 11 is, as shown in FIG. 2(a), formed on an outer end surface of the solid electrolyte body 10 within a range of 80% of the length L of a gas-exposed portion 115 of the oxygen sensing element 1 and has a length M that is equal to 0.69 L. The thickness of the head electrode 11 is 1.5 μm.

The solid electrolyte body 10 includes a base portion 119.

The base portion 119 has formed thereon a base electrode 12 having a thickness of 0.5 μm which is smaller than that of the head electrode 11. The base electrode 12 and the head electrode 11 may be made by chemical plating, chemical vapor deposition, physical vapor deposition, sputtering, or application of an organic metallic complex.

The oxygen sensing element 1 is so designed that a difference between output voltages produced at an ambient temperature of 400° C. when λ (excess air factor)=0.9 (rich side) and when λ=1.1 (lean side) is greater than or equal to 0.65 V.

The oxygen sensing element 1, as clearly shown in FIG. 1, defines within the solid electrolyte body 10 an atmospheric chamber 15 within which a ceramic heater 19 is disposed. The ceramic heater 19 heats the oxygen sensing element 1 up to an activating temperature quickly. An inner electrode 13 is formed on an inner wall of the solid electrolyte body 10 within the atmospheric chamber 15. The oxygen sensing element 1 of this invention is, as described above, designed to measure an oxygen content in gases using the oxygen concentration dependent electromotive force or the limiting current. Specifically, the measurement of the oxygen content using the oxygen concentration dependent electromotive force is achieved by determining a difference in output voltage between the inner electrode 13 and an outer electrode (i.e., the base electrode 12 and the head electrode 11) which depends upon the concentration of oxygen in the gasses. The measurement of the oxygen content using the limiting current is achieved by applying a given voltage across the inner electrode 13 and the outer electrode to pick up a limiting current which depends upon the concentration of oxygen in the gasses. These techniques are known in the art, and explanation thereof in detail will be omitted here.

The head electrode 11 has a two-layer stracture and is made of a lamination comprising an inner layer 111 and an outer layer 112. The base electrode 12 has a single-layer structure and consists of part the outer layer 112 only.

The solid electrolyte body 10, as clearly shown in FIGS. 2(a) and 2(b), has formed thereon a flanged portion 16 with a tapered surface 161. The tapered surface 161 engages a housing 30 of an oxygen sensor 3, as will be discussed later in detail with reference to FIG. 3, when the oxygen sensing element 1 is installed in the housing 30. Specifically, a portion of the oxygen sensing element 1 beneath the tapered surface 161 corresponds to the gas-exposed portion 115.

Disposed on outer surfaces of the head electrode 11 and the base electrode 12 is a protective layer 18 which may be made of two layers: a first layer formed in thermal spraying using spinel and a second layer made of alumina. Although not illustrated, the oxygen sensing element 1 has output terminals and leads or conductive portions communicating with the output terminals and the above described electrodes.

Figure 3:
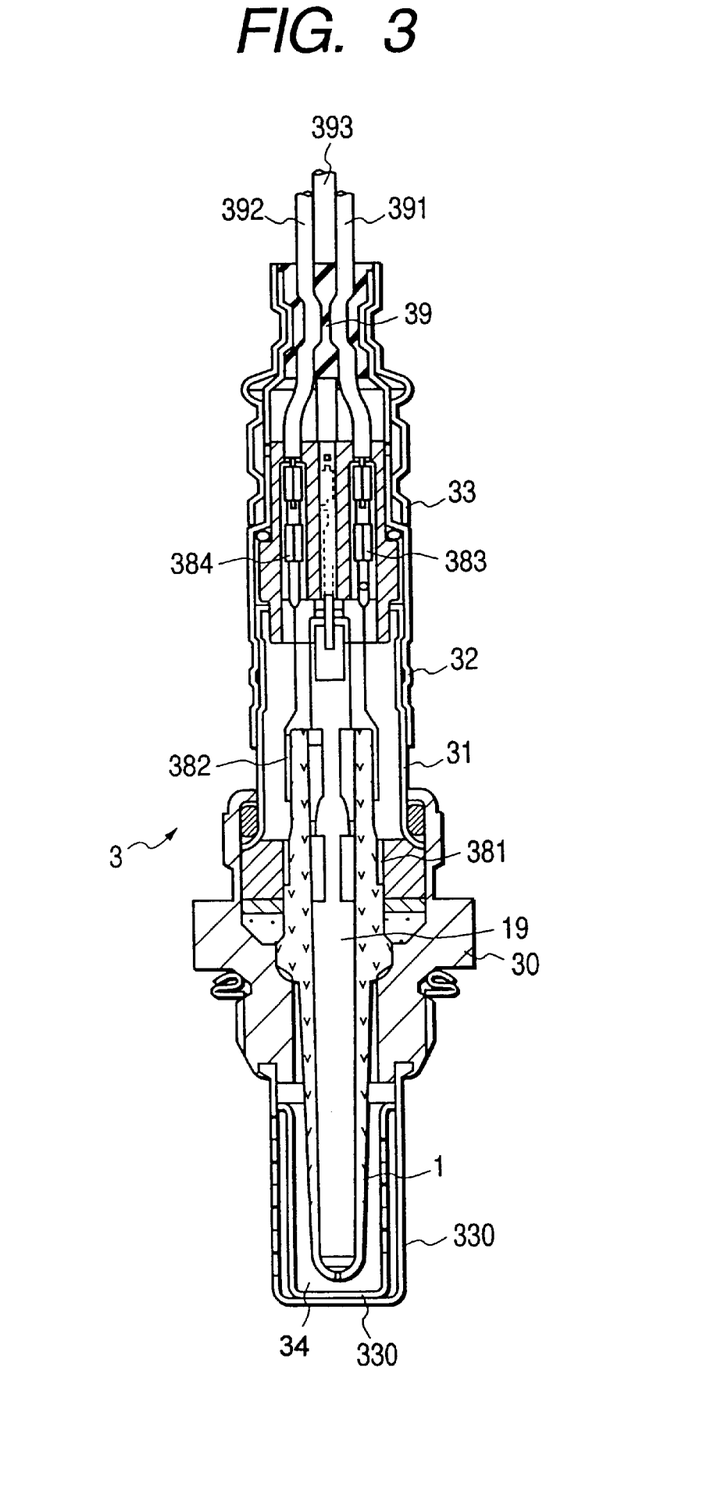
FIG. 3 is a vertical cross sectional view which shows an oxygen sensor in which the oxygen sensing element of FIG. 1 is installed.

FIG. 3 shows the oxygen sensor 3 in which the oxygen sensing element 1 is installed.

The oxygen sensor 3 includes generally the housing 30 into which the oxygen sensing element 1 is inserted. A double-walled cover 330 is mounted on the bottom of the housing 30 to protect the head portion 110 of the oxygen sensing element 1 and defines therein a gas chamber 34. The oxygen sensor 3 also includes three cylindrical covers 31, 32, and 33 exposed to air.

The ceramic heater 19 made of a ceramic bar member is, as already discussed, disposed within the atmospheric chamber 15 with a given clearance between itself and the inner wall of the atmospheric chamber 15.

An elastic insulating member 39 through which leads 391, 392, and 393 pass is fitted into an end opening of the cover 32. The leads 391 and 392 pick up sensor signals produced in the solid electrolyte body 10 and output them to an external device. The lead wire 393 supplies the power to the ceramic heater 19.

Terminal connectors 383 and 384 are disposed inside the cover 32 and connect the leads 391 and 392 with terminals 381 and 382 which lead to terminals (not shown) mounted on the oxygen sensing element 1.

In a manufacturing process of the oxygen sensing element 1, a zirconia material is first shaped to a cup, as shown in FIGS. 1, 2(a), and 2(b), and then baked to produce the solid electrolyte body 10. Platinum cores are precipitated on inner and outer walls of the solid electrolyte body 10 in deoxidization using a chloroplatinic acid solution and a reducer and then dried.

Subsequently, the thus formed solid electrolyte body 10 is dried. The platinum cores are plated chemically with platinum to form thin films having a thickness of 0.5 μm and then baked at 1000° C. for one hour to produce the inner layer 111 and the inner electrode 13.

As an alternative to forming the inner electrode 13 together with the inner layer 111 in the above manner, the inner electrode 13 may be formed at the same time that the outer layer 112 is formed or that the outer and inner layers 112 and 111 are formed.

In the same manner as that to produce the inner layer 111 and the inner electrode 13, the outer layer 112 having a thickness of 1.0 μm is formed over the inner layer 111 and a portion of the outer surface of the solid electrolyte body 10 adjacent the inner layer 111 to produce the two-layer head electrode 11 and the single-layer base electrode 12.

Finally, a porous layer made of alumina spinel is formed in plasma spraying over the head electrode 111 and the base electrode 12 to produce the protective layer 18.

As an alternative to baking the solid electrolyte body 10 after the thin films are formed on the inner and outer walls of the solid electrolyte body 10 for producing the inner layer 111 and the inner electrode 13, the solid electrolyte body 10 may be baked after the inner layer 111 and the remaining outer surface of the solid electrolyte body 10 are chemically plated to form the outer layer 112. Specifically, platinum cores are formed in the same manner as that to make the inner layer 111 and the inner electrode 13 on a portion of the outer surface of the solid electrolyte body 10 on which the inner layer 111 and the outer layer 112 are to be formed.

The solid electrolyte body 10 is then immersed in a plating bath fully to build up a deposit having a thickness of 1.0 μm on the outer surface of the solid electrolyte body 10. Next, the solid electrolyte body 10 is withdrawn partly from the plating bath so as to expose the base portion 119 to air, leaving only the head portion 110 in the plating bath to build up an additional deposit having a thickness of 0.5 μm and baked to produce the head electrode 11 and the base electrode 12.

Figure 5:
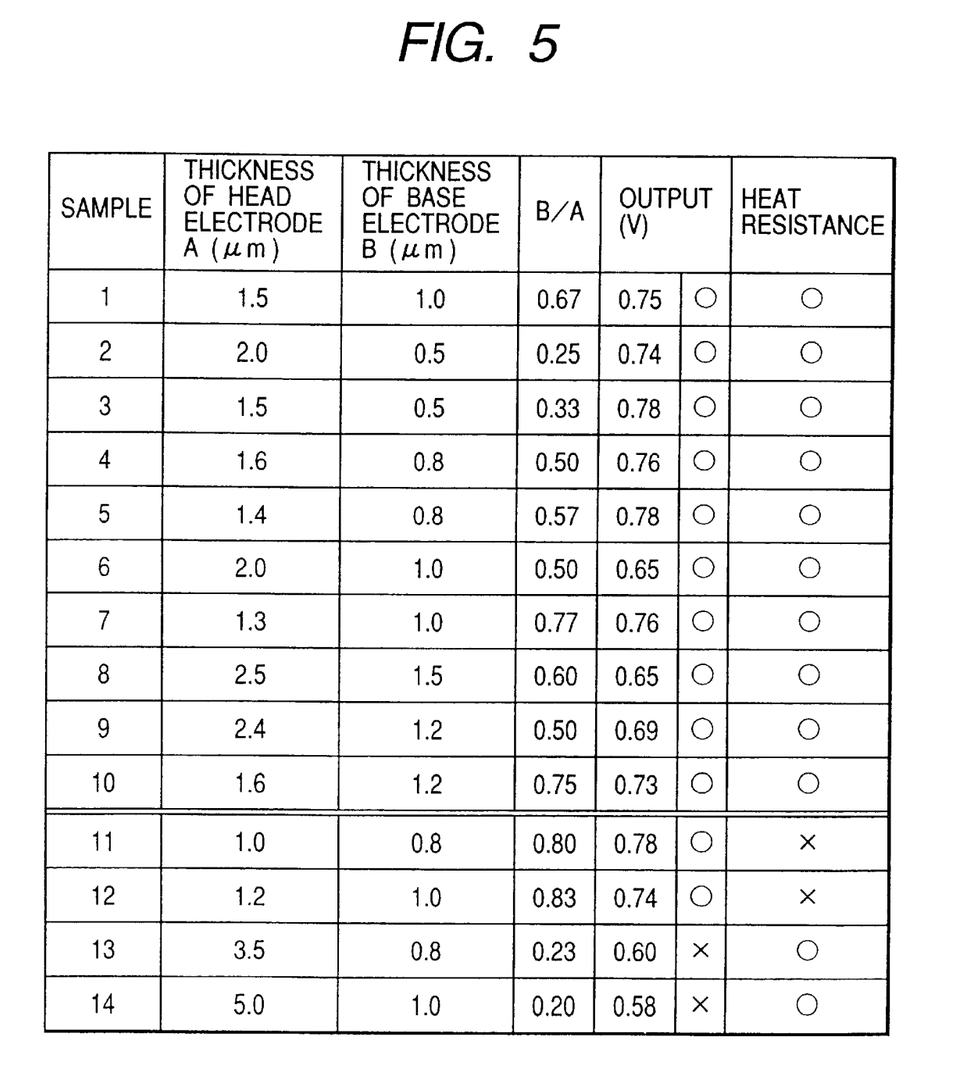
FIG. 5 is a table which represents electrical and physical properties of oxygen sensing element samples which have the same structure as the one shown in FIG. 1 and on which a head electrode and a base electrode having different thicknesses within ranges 1.0 μm to 5.0 μm and 0.5 μm to 1.5 μm are formed.

FIG. 5 is a table representing electrical and physical properties of the oxygen sensing element 1 of the invention. Sample Nos. 1 to 14 indicate oxygen sensing elements which have the same structure as the one shown in FIGS. 1, 2(a), and 2(b) and on which the head electrode 11 and the base electrode 12 having different thicknesses within ranges 1.0 μm to 5.0 μm and 0.5 μm to 1.5 μm are formed. Outputs (V) represent differences in voltage outputted from the samples Nos. 1 to 14 measured at an ambient temperature of 400° C. when λ (excess air factor)=0.9 (rich side) and λ=1.1 (lean side). Some of the sample Nos. 1 to 14 whose output voltage differences are greater than 0.65 V are indicated by "O".

The heat-resistance tests were performed for all the samples at 900° C. for 500 hours. After the tests, the degree of aggregation of the head electrode 11 was measured in image analysis using an SEM to determine an open porosity of the head electrode 11. Some of the sample Nos. 1 to 14 whose open porosities are less than 50% are indicated by "O". The open porosity less than 50% shows a smaller degree of aggregation of the head electrode 11 demonstrating a higher heat-resistance.

The table in FIG. 5 shows that sample Nos. 1 to 10 produce higher output voltages and have higher heat-resistances, while sample Nos. 11 and 12 have lower heat-resistances, and sample Nos. 13 and 14 produce lower output voltages. Specifically, it is found that the oxygen sensing element, in which the head electrode 11 has the thickness ranging from 1.2 to 3.0 μm, the base electrode 12 has the thickness ranging from 0.3 to 2.4 μm, and a thickness ratio (the thickness of the base electrode 12/the thickness of the head electrode 11) is within a range from 0.25 to 0.8, provides a higher output voltage and shows a higher heat-resistance.

The head electrode 11 is, as described above, disposed over a limited end area of the gas-exposed portion 115 across the head portion 110.

A portion of the solid electrolyte body 10 on which the head electrode 11 is mounted, as can be seen in FIG. 4, shows high surface temperatures which are uniform in distribution, thereby resulting in substantially a constant output from the oxygen sensing element 1. Specifically, the oxygen sensing element 1 of the invention provides an output that is proportional to the concentration of oxygen precisely.

The head electrode 11 is smaller in thickness than the base electrode 12. As can be seen from FIG. 4, the smaller the thickness of the electrode of the oxygen sensing element, the smaller a difference in output between the head portion 110 and the base portion 119. The thinned electrode, however, gives rise to a problem that the heat-resistance is low. In order to alleviate the problem, the oxygen sensing element 1 of the invention has the thick head electrode 11 formed on the end portion requiring a higher heat-resistance, ranging from the tip to 0.69 L and the thin base electrode 12 formed on an adjacent portion above 0.69 L which has a thickness allowing the base portion 119 to produce an output voltage substantially equal to that produced by the base electrode 12. Therefore, the oxygen sensing element 1 of the invention provides an output, as indicated by a dashed line in FIG. 4, at the head portion 110 (α in FIG. 4) located ahead of a boundary defined at an interval of 0.69 L away from the tip of the oxygen sensing element 1 and an output, as indicated by a dotted line, at the base portion 119 (β in FIG. 4) located behind the boundary.

Figure 6A:
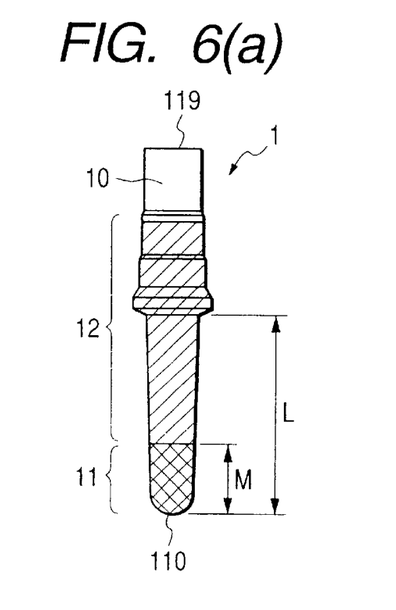
FIGS. 6(a) and 6(b) are perspective views which show the first and second modifications of the oxygen sensing element of FIG. 1.
Figure 6B:
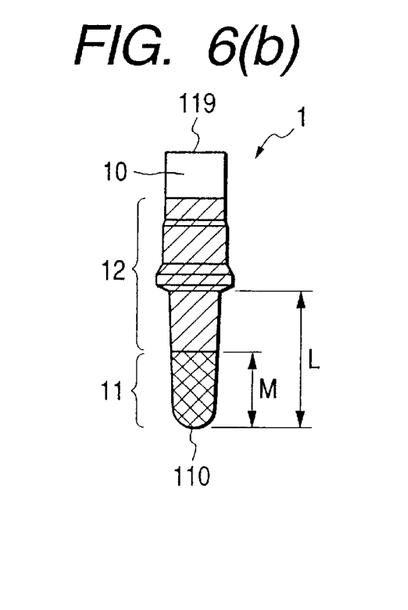

FIGS. 6(a) and 6(b) show first and second modifications of the oxygen sensing element 1. The oxygen sensing element 1 of FIG. 6(a) has the head electrode 11 whose length M is 0.34 L, while the oxygen sensing element 1 of FIG. 6(b) has a total length (from the head portion 110 to the base portion 119) shorter than that in FIG. 6(a) and includes the head electrode 11 whose length M is 0.59 L.

Figure 7A:
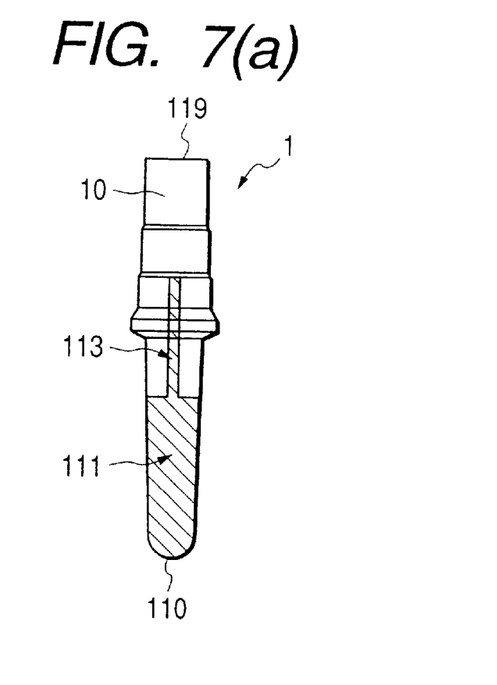
FIGS. 7(a) and 7(b) are perspective views which show the third modification of the oxygen sensing element of FIG. 1.
Figure 7B:
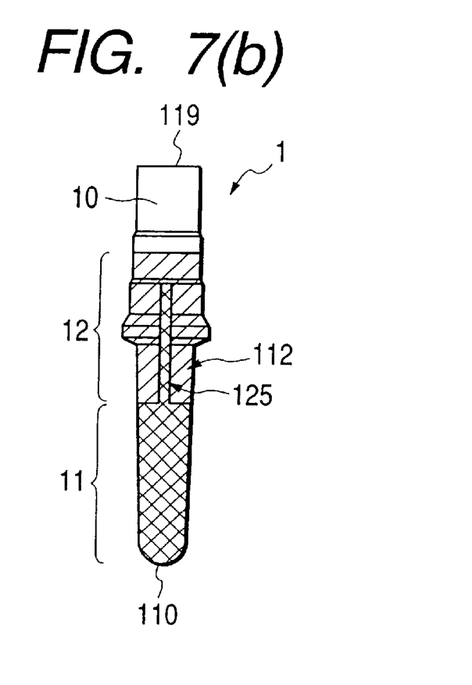

FIGS. 7(a) and 7(b) show a third modification of the oxygen sensing element 1. The oxygen sensing element 1 has, as shown in FIG. 7(b), a conductive lead 125 formed inside the base electrode 12 (i.e., the outer layer 112). The conductive lead 125 is, as shown in FIG. 7(a), made of an extension 113 of the inner layer 111 and has a thickness greater than that of the base electrode 12 so that it has a smaller electric resistance for ensuring picking up of an output from the head electrode 11.

The second embodiment of the invention will be discussed below which uses an organic metallic complex in producing the oxygen sensing element 1.

First, a zirconia material is shaped to a cup, as shown in FIGS. 1, 2(a), and 2(b), and then baked to produce the solid electrolyte body 10. An organic metallic paste or a solution (solvent: Terpineol) containing a benzylidene platinum compound or balsam platinum that is an organic metallic complex is prepared and applied to the inner and outer walls of the solid electrolyte body 10 using screen printing, pad printing, or roll transferring techniques.

Subsequently, the thus formed solid electrolyte body 10 is subjected to heat treatment at 1000° C. to precipitate platinum layers having a thickness of 0.5 μm on the solid electrolyte body 10, thereby producing the inner layer 111 and the inner electrode 13.

In the same manner as that to produce the inner layer 111 and the inner electrode 13, the outer layer 112 having a thickness of 1.0 μm is formed over the inner layer 111 and a portion of the outer surface of the solid electrolyte body 10 adjacent the inner layer 111 to produce the two-layer head electrode 11 and the single-layer base electrode 12.

Other steps are identical with those of the first embodiment, and explanation thereof in detail will be omitted here.

The inner electrode 13 may be formed at the same time that the outer layer 112 is formed or that the outer and inner layers 112 and 111 are formed.

The organic metallic paste or solution may be applied to the solid electrolyte body 10 to form coats having a required thickness in the pad printing, for example, and dried, after which the solid electrolyte body 10 is baked to produce the base electrode 12 and the head electrode 11 together with the inner electrode 13.

Figure 8A:
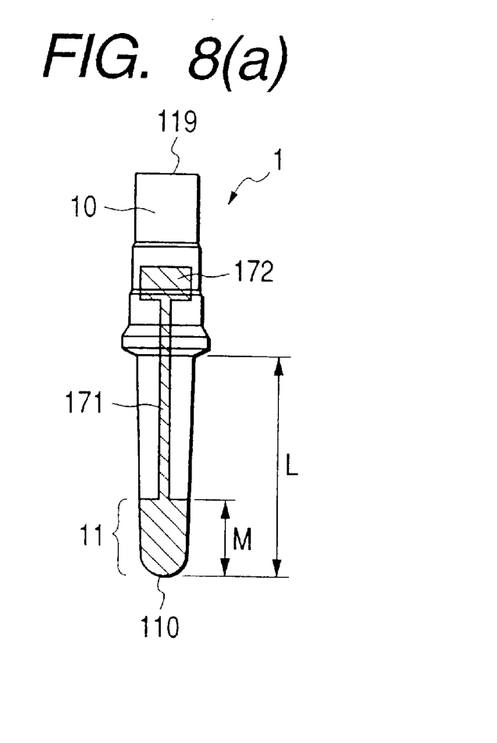
FIG. 8(a) is a perspective view which shows the fourth modification of the oxygen sensing element of FIG. 1.
Figure 8B:
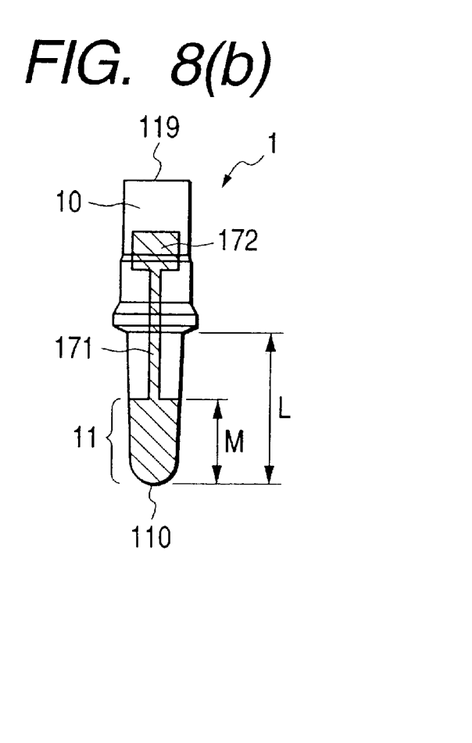
FIG. 8(b) is a perspective view which shows the fifth modification of the oxygen sensing element of FIG. 1.
Figure 9:
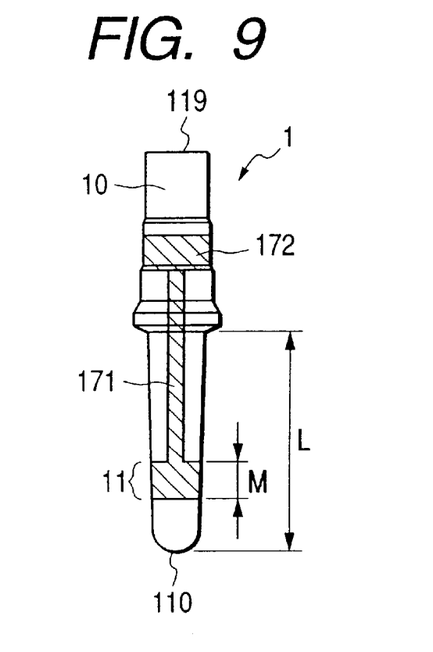
FIG. 9 is a perspective view which shows the sixth modification of the oxygen sensing element of FIG. 1.

FIGS. 8(a), 8(b), and 9 show fourth to sixth modifications of the oxygen sensing element 1 each of which has only the head electrode 11 disposed on the outer surface of the solid electrolyte body 10.

The oxygen sensing element 1 in FIG. 8(a) has the head electrode 11 whose length M is 0.34 L. A terminal 172 which connects with the head electrode 11 through a lead 171 is mounted on a peripheral surface of the base portion 119 for picking up an output of the head electrode 11.

The oxygen sensing element 1 in FIG. 8(b) is identical in structure with the one shown in FIG. 8(a), but different therefrom in that the length M of the head electrode 11 is 0.59 L.

The oxygen sensing element 1 in FIG. 9 includes the head electrode 11 made of a hollow cylindrical layer having the length M that is 0.23 L. The head electrode 11 connects with the terminal 172 through the lead 171 and is located at an interval of 0.59 L away from the tip of the solid electrolyte body 10.

The lead 171 and the terminal 172 in FIGS. 8(a) to 9 may be made using a platinum paste.

Figure 10A:
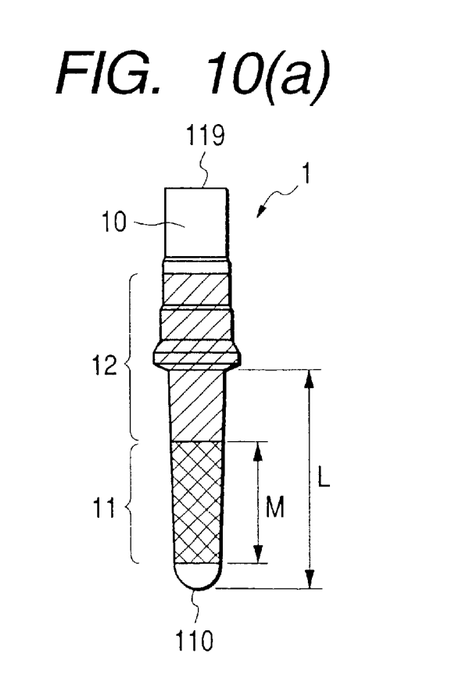
FIG. 10(a) is a perspective view which shows the seventh modification of the oxygen sensing element of FIG. 1.
Figure 10B:
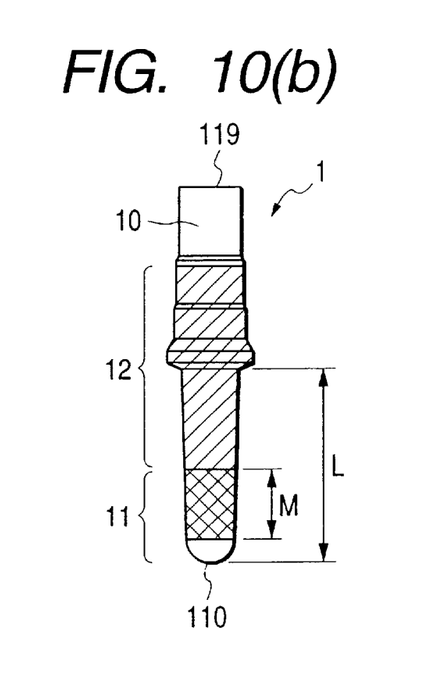
FIG. 10(b) is a perspective view which shows the eighth modification of the oxygen sensing element of FIG. 1.

FIGS. 10(a) and 10(b) show seventh and eighth modifications of the oxygen sensing element 1 each of which has the head electrode 11 made of a hollow cylindrical layer.

The oxygen sensing element 1 in FIG. 10(a) has formed thereon the base electrode 12 and the head electrode 11 having the length M that is 0.56 L. A lower end, as viewed in the drawing, of the head electrode 11 is located at an interval of 0.69 L away from the tip of the solid electrolyte body 10.

The oxygen sensing element 1 in FIG. 10(b) is identical in structure with the one shown in FIG. 10(a), but different therefrom in that the head electrode 11 has the length M that is 0.37 L and is located at the lower end at an interval of 0.47 L away from the tip of the solid electrolyte body 10.

As apparent from the above, no electrode is formed on the head portion 110 where an electrode intends to aggregate, thereby minimizing a change in sensor performance due to the deterioration of durability.

While the present invention has been disclosed in terms of the preferred embodiment in order to facilitate a better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. An oxygen sensing element for measuring an oxygen content in gases comprising:

a cup-shaped solid electrolyte body having a sensing portion to be disposed within the gases for measurement of the oxygen content, the sensing portion having a given length;

an inner electrode formed on an inner wall of said solid electrolyte body to provide an output signal; and an outer electrode formed on an outer wall of the sensing portion of said solid electrolyte body to provide an output signal for determining the oxygen content in the gases based on the output signals from said inner and outer electrodes, said outer electrode including a head section and a base section, said head section occupying an area on the outer wall of said solid electrolyte body within a range of 80% of the given length of the sensing portion of said solid electrolyte body and having a thickness ranging from 1.2 to 3.0 μm, said base section being formed on a portion of the outer wall of said solid electrolyte body adjacent to said head section and extending outside the sensing portion, said base section having a thickness smaller than that of said head section.

2. An oxygen sensing element as set forth in claim 1, wherein the thickness of said base section is within a range from 0.3 to 2.4 μm.

3. An oxygen sensing element as set forth in claim 1, wherein a ratio of the thickness of said base section to the thickness of said head section is within a range of 0.25 to 0.8.

4. An oxygen sensing element as set forth in claim 1, wherein the area of the outer wall of said solid electrolyte body on which said outer electrode is formed covers a head of the sensing portion.

5. An oxygen sensing element as set forth in claim 4, wherein said base section is formed far from the head of the sensing portion across said head section.

6. An oxygen sensing element as set forth in claim 1, wherein said head section is comprised of at least two layers.

7. An oxygen sensing element as set forth in claim 6, wherein said base section is made from at least one of said at least two layers.

8. An oxygen sensing element as set forth in claim 1, wherein the output signal is an electromotive force across said inner and outer electrodes which varies as a function of the oxygen content of the gases in which the sensing element is disposed.

9. An oxygen sensing element for measuring an oxygen content in gases comprising:

a cup-shaped solid electrolyte body having a sensing portion to be disposed within the gases for measurement of the oxygen content, the sensing portion having a given length and an end thereof;

an inner electrode formed on an inner wall of said solid electrolyte body to provide an output signal; and an outer electrode formed on an outer wall of the sensing portion of said solid electrolyte body to provide an output signal for determining the oxygen content in the gases based on the output signals from said inner and said outer electrodes, the output signal being an electromotive force across said inner and outer electrodes which varies as a function of the oxygen content in the gases in which the sensing element is disposed, said outer electrode comprising a head section that includes an inner layer and an outer layer in electrical contact with each other, said inner layer occupying a region on the outer wall of said solid electrolyte body that extends from the end of the sensing portion by a distance that is less than or equal to 80% of the given length of the sensing portion of said solid electrolyte body, said head section having a thickness ranging from 1.2 to 3.0 $\mu$m.

10. An oxygen sensing element as set forth in claim 9, wherein the area of the outer wall of said solid electrolyte body on which said outer electrode is formed covers a head of the sensing portion.

11. An oxygen sensing element as set forth in claim 9, wherein said outer electrode further comprises a base section which is formed on a portion of the outer wall of said solid electrolyte body adjacent to said head section and which has a thickness smaller than that of said head section, the thickness of said base section being within a range from 0.3 to 2.4 $\mu$m.

12. An oxygen sensing element as set forth in claim 9, wherein said outer electrode further comprises a base section which is formed on a portion of the outer wall of said solid electrolyte body adjacent to said head section and which has a thickness smaller than that of said head section, a ratio of the thickness of said base section to the thickness of said head section being within a range of 0.25 to 0.8.

13. An oxygen sensing element as set forth in claim 9, wherein said outer electrode further comprises a base section which is formed on a portion of the outer wall of said solid electrolyte body adjacent to said head section and which has a thickness smaller than that of said head section, said base section being formed far from the head of the sensing portion across said head section.

14. An oxygen sensing element for measuring an oxygen content in gases comprising:

a cup-shaped solid electrolyte body having a sensing portion to be disposed within the gases for measurement of the oxygen content, the sensing portion having a given length and an end;

an inner electrode formed on an inner wall of said solid electrolyte body to provide an output signal; and an outer electrode formed on an outer wall of the sensing portion of said solid electrolyte body to provide an output signal for determining the oxygen content in the gases based on the output signals from said inner and said outer electrodes, the output signal being an electromotive force across said inner and outer electrodes which varies as a function of the oxygen content of the gases in which the sensing element is disposed, said outer electrode comprising a head section occupying a region on the outer wall of said solid electrolyte body that extends from the end of the sensing portion by a distance that is less than or equal to 80% of the given length of the sensing portion of said solid electrolyte body, said head section having a thickness ranging from 1.2 to 3.0 $\mu$m, wherein said outer electrode further comprises a base section which is formed on a portion of the outer wall of said solid electrolyte body adjacent to said head section and which has a thickness smaller than that of said head section.

15. An oxygen sensing element as set forth in claim 14, wherein the thickness of said base section is within a range from 0.3 to 2.4 $\mu$m.

16. An oxygen sensing element as set forth in claim 14, wherein a ratio of the thickness of said base section to the thickness of said head section is within a range of 0.25 to 0.8.

17. An oxygen sensing element as set forth in claim 14, wherein said base section is formed far from the head of the sensing portion across said head section.

18. An oxygen sensing element as set forth in claim 14, wherein said outer electrode further comprises a base section which is formed on a portion of the outer wall of said solid electrolyte body adjacent to said head section and which has a thickness smaller than that of said head section, the area of the outer wall of said solid electrolyte body on which said outer electrode is formed covering a head of the sensing portion.

* * * * *